United States Patent
Knochel et al.

(10) Patent No.: US 11,236,113 B2
(45) Date of Patent: Feb. 1, 2022

(54) HYDROCARBON-SOLUBLE HALOGEN AND THIOLATE/MAGNESIUM EXCHANGE REAGENTS

(71) Applicants: ALBEMARLE GERMANY GMBH, Frankfurt am Main (DE); Ludwig-Maximilians-Universität München, Munich (DE)

(72) Inventors: Paul Knochel, Munich (DE); Dorothée Ziegler, Munich (DE); Meike Simon, Burghausen (DE)

(73) Assignee: Albemarle Germany GmbH, Frankfurt am Main (DE)

( * ) Notice: Subject to any disclaimer, the term of this patent is extended or adjusted under 35 U.S.C. 154(b) by 0 days.

(21) Appl. No.: 16/651,790

(22) PCT Filed: Sep. 20, 2018

(86) PCT No.: PCT/EP2018/075506
§ 371 (c)(1),
(2) Date: Mar. 27, 2020

(87) PCT Pub. No.: WO2019/063418
PCT Pub. Date: Apr. 4, 2019

(65) Prior Publication Data
US 2020/0239496 A1 Jul. 30, 2020

(30) Foreign Application Priority Data

Sep. 27, 2017 (DE) .................... 10 2017 217 230.4
Jan. 18, 2018 (DE) .................... 10 2018 200 805.1

(51) Int. Cl.
*C07B 49/00* (2006.01)
*C07F 3/02* (2006.01)
*C07C 41/22* (2006.01)
*C07C 41/60* (2006.01)
*C07D 211/16* (2006.01)
*C07C 29/70* (2006.01)
*C07C 41/14* (2006.01)
*C07F 1/02* (2006.01)

(52) U.S. Cl.
CPC ................ *C07F 3/02* (2013.01); *C07B 49/00* (2013.01); *C07C 29/70* (2013.01); *C07C 41/22* (2013.01); *C07C 41/60* (2013.01); *C07D 211/16* (2013.01); *C07C 41/14* (2013.01); *C07F 1/02* (2013.01)

(58) Field of Classification Search
CPC ... C07B 49/00; C07F 3/02; C07F 1/02; C07C 41/14; C07C 41/22; C07C 31/30; C07C 29/70; C07D 211/16
See application file for complete search history.

(56) References Cited

U.S. PATENT DOCUMENTS 4,634,786 A * 1/1987 Kamienski .............. C07C 29/70
260/665 R
7,384,580 B2 * 6/2008 Knochel ................. C07B 49/00
260/665 G

FOREIGN PATENT DOCUMENTS

EP 1 582 524 A1 10/2005

OTHER PUBLICATIONS

Heitz, Stephan, et al., "Molecular Heterobimetallic Approach to Li-Containiiig MgO Nanoparticles with Variable Li-Concentrations Using Lithium-Methylmagnesium Alkoxide Clusters", Chemistry of Materials, vol. 22, No. 16, Aug. 24, 2010 (Aug. 24, 2010), pp. 4563-4571.
Zaragoza-Calero, Silvia, et al., "Solid state and solution studies of lithium tris(n-butyl)magnesiates stabilised by Lewis donors" Dalton Transactions, GB, vol. 44, No. 16, Jan. 1, 2015 (Jan. 1, 2015), pp. 7258-7267.
Ziegler, Dorothee S., et al., "Generation of Aryl and Heteroaryl Magnesium Reagents in Toluene by Br/Mg or Cl/Mg Exchange", Angewandte Chemie International Edition, vol. 57, No. 22, Apr. 14, 2018 (Apr. 14, 2018), pp. 6701-6704, XP055519292.
Ziegler Dorothee S., "Metalation and Functionalization of Pyridones, Naphthyridones and Pyrones Using TMP-Bases and Generation of Aryl and Heteroaryl Magnesium Reagents in Toluene by Br/Mg- and Cl/Mg-Exchange", dissertation to obtain the doctoral degree, Oct. 16, 2018 (Oct. 16, 2018), pp. 1-184, XP055780326, Munich.

* cited by examiner

*Primary Examiner* — Yate' K Cutliff
(74) *Attorney, Agent, or Firm* — R. Andrew Patty, II; McGlinchey Stafford, PLLC

(57) ABSTRACT

The invention relates to hydrocarbon-soluble halogen or thiolate/magnesium exchange reagents of the general formula $R^1MgR^1_{1-n}(OR^3)_n \cdot LiOR2 \cdot (1-n)LiOR^3 \cdot a\text{Donor}$ in which: $R^1$ is a C1-C8 alkyl and $OR^2$ as well as $OR^3$ are same or different and represent primary, secondary, or tertiary alkoxide residues having 3 to 18 carbon atoms, wherein $R^2$ and/or $R^3$ can for their part contain an alkoxy substituent $OR^4$; a assumes a value of 0 to 2, n assumes a value between 0 and 1, and the donor is an organic molecule containing at least 2 nitrogen atoms.

15 Claims, 4 Drawing Sheets

HYDROCARBON-SOLUBLE HALOGEN AND THIOLATE/MAGNESIUM EXCHANGE REAGENTS

CROSS-REFERENCE TO RELATED APPLICATIONS

This application is the National Stage of International Patent Appl. No. PCT/EP2018/075506 filed on Sep. 20, 2018, which application claims priority from German Patent Application No. 102017217230.4, filed on Sep. 27, 2017, and German Patent Application No. 102018200805.1, filed on Jan. 18, 2018. Each patent application identified above is incorporated here by reference in its entirety.

FIELD

The invention relates to hydrocarbon-soluble reagents for the exchange of halogen or thiolate functions in aromatics or heteroaromatics for magnesium.

BACKGROUND

Organomagnesium halides play an important part as key intermediates in organic synthesis. Since their discovery by Victor Grignard, these compounds are of vital importance in modern organic synthesis. They are typically prepared by direct insertion of magnesium in the form of magnesium chips, activated magnesium powder, or by magnesium chips in the presence of lithium chloride. The heterogeneous nature of these reactions, however, complicates the transfer from the laboratory to large-scale production and industrial use. Functionalized Grignard compounds often cannot be prepared in this manner, since functional groups such as nitriles or esters would be attacked and decomposed. Direct magnesation of arenes and heteroarenes can be achieved by using hindered magnesium amides which are highly soluble in THF, such as TMPMgCl.LiCl or $TMP_2Mg.2LiCl$ (TMP=2,2,6,6-tetramethyl piperidyl). Alternatively, organomagnesium halides can be prepared by a halogen-magnesium exchange by means of reacting aryl or heteroaryl iodides or bromides with specific alkyl magnesium halides (Rieke, D. R., Sell, M. S. In Handbook of Grignard reagents (Eds.: G. S. Silvermann, P. E. Rakita) 1996) or, even better, with the turbo-Grignard reagent (i-PrMgCl.LiCl) (Krasvoskiy, A.; Knochel P.; Angew. Chem. Int. Ed. 2004, 43, 3333). The turbo-Grignard reagents are available as solutions in ether-containing solvents (THF, etc.), and subsequent reactions are also performed using ether-based solvents.

Only few methods for the synthesis of organomagnesium compounds in apolar solvents (hydrocarbons) are known (Chtcheglova, L.; Carlotii, S.; Deffieux, A.; Poirier, N.; Barbier, M.; Fr Demanden 2003, FR 2840901A1; 20031219, and Baillie, E. S.; Bluemke, T. D.; Clegg, W.; Kennedy, A. R.; Klett, J.; Russo, L.; de Tullio, M.; Hevia E. Chem. Comm. 2014, 50, 12859). For example, dialkyl magnesium compounds ($R_2Mg$) are prepared by direct insertion of magnesium into the C-halogen bonds of long-chain alkyl halides which have a branch in the alpha position. It is further known that mixed potassium-magnesium ate complexes with silyl substituents $(Me_3SiCH_2)_3MgK$—prepared in benzene—can be used as strong bases for the generation of aryl magnesiates in hexane (Hevia, E. Chem. Commun. 2014, 50, 12859).

Exchange reagents composed of RMgHal (R=alkyl, aryl; Hal=halogen selected from Cl, Br, I) are unknown in hydrocarbon-based solvents which are free of donor solvents. Instead, it is known that Grignard compounds are at an equilibrium with their disproportionation products, $R_2Mg$ and $MgCl_2$, according to $$2RMgHal \rightarrow R_2Mg + MgHal_2$$

("Schlenk equilibrium"), wherein the equilibrium state depends on the donor number of the solvent. In donor-free solvents, that is, hydrocarbons, the dissociation products dialkyl magnesium and magnesium halide are virtually exclusively present, wherein $MgHal_2$ precipitates due to its insolubility. Halogen/magnesium exchange reagent solutions in apolar solvents would be of great industrial interest. Apart from the fact that hydrocarbons are among the most inexpensive solvents, the use of hydrocarbon solvents simplifies product conditioning significantly and improves recycling of the non-water-soluble solvent during aqueous treatment. Hydrocarbons (HCs), unlike tetrahydrofuran (THF), for example, are not soluble in, or miscible with, water, such that the mostly organosoluble products can be easily separated.

Furthermore, the aqueous phases are therefore charged with very low concentrations of organic compounds, which positively affects environmental compatibility.

Document EP1582524B1 describes reagents of the general formula $R*(MgX)_n.LiY$, wherein:

n is 1 or 2;

R* is substituted or non-substituted $C_4$-$C_{24}$ aryl or $C_3$-$C_{24}$ heteroaryl, which contains one or several heteroatoms, such as B, O, N, S, Se, P, F, Cl, Br, I, or Si; a linear or branched, substituted or non-substituted $C_1$-$C_{20}$ alkyl, $C_2$-$C_2$O-alkenyl, or $C_2$-$C_{20}$ alkinyl; or substituted or non-substituted $C_3$-$C_{20}$ cycloalkyl; X and Y independently of each other, or each, are Cl, Br, or I, preferably Cl; HalOn (wherein n=3, 4); carboxyl of the formula $RCO_2$; alkoxide, or phenocide of the formula RO; dialkoxide of the formula LiO—R—O; disilazide of the formula $(R_3Si)_2N$; thiolate of the formula SR; $RP(O)O_2$; or SCOR; wherein R is like R* defined above;

linear or branched, substituted or non-substituted $C_1$-$C_{20}$ alkyl, or $C_3$-$C_{20}$ cycloalkylamine of the formula RNH; dialkyl/arylamine of the formula $R_2N$ (wherein R is as defined above or $R_2N$ represents a heterocyclic alkylamine); phosphine of the formula $PR_2$ (wherein R is as defined above or $PR_2$ is a heterocyclic phosphine); $O_nSR$ (wherein n=2 or 3 and R is as defined above); or $NO_n$ (wherein n=2 or 3); or X=R* as defined above.

The patent document describes mixtures of organomagnesium compounds and lithium salts as solutions in organic donor solvents. While hydrocarbons are also claimed as solvents therein, it is not shown how such HC soluble products of the general formula $R*(MgX)_n.LiY$ can be prepared and what specific uses there are.

It is the problem of the invention to indicate hydrocarbon-soluble reagents for exchanging halogen or thiolate for magnesium, methods for their production and their use, wherein these reagents are to be particularly usable for the metalation of such substrates which according to prior art cannot be magnesated by means of the halogen/magnesium exchange principle. These are, first of all, electron-rich aromatics and heteroaromatics. Furthermore, special embodiments of the hydrocarbon-soluble exchange-active compounds must be capable of magnesating slightly reactive substrates such as chloroaryls or thiolatoaryls by exchanging the chlorine or thiolate function.

DESCRIPTION

Figure 1:
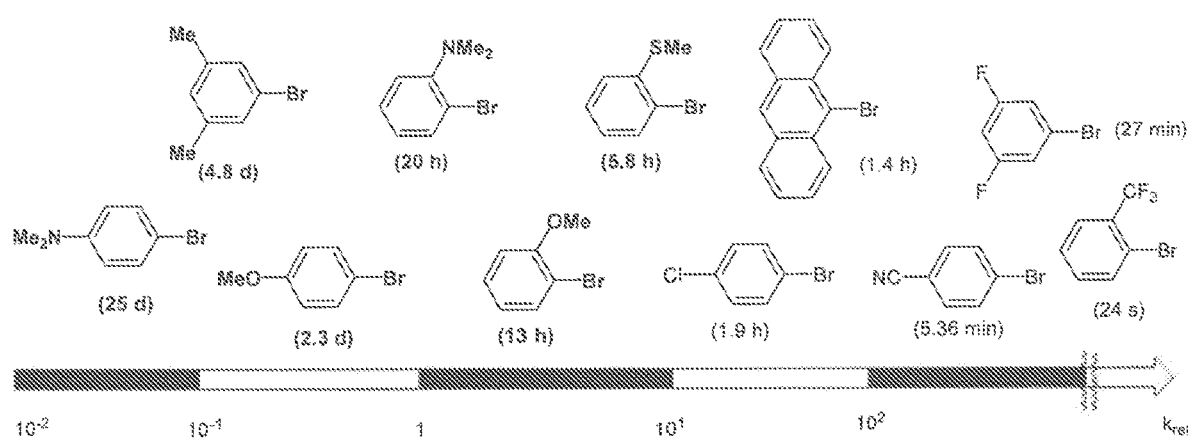
FIG. 1 depicts relative reactivities of substituted bromobenzenes with i-PrMgCl.LiCl in THF solution at 0° C.

According to the invention, the problem is solved by hydrocarbon-soluble reagents of the general formula $R^1MgR^1_{1-n}(OR^3)_n.LiOR^2.(1-n)LiOR^3.a$Donor, wherein: $R^1$ is a $C_1$-$C_8$ alkyl and $OR^2$ as well as $OR^3$ are same or different and represent primary, secondary, or tertiary alkoxy groups having 3 to 18 carbon atoms, wherein $R^2$ and/or $R^3$ can for their part contain an alkoxy substituent $OR^4$; a assumes a value of 0 to 2, n assumes any value from 0 to 1, and the donor is an organic molecule containing at least two nitrogen atoms. It is preferred that n has the value 0 or 1. These compounds are generally capable of exchanging halogen or thiolate functions for magnesium. It was surprisingly found that exchange reagents according to the invention wherein n=1 display a good to excellent solubility in hydrocarbons while maintaining their Grignard-analogous structure and composition and therefore do not disproportionate according to $2R^1MgOR^3.LiOR^2.a$Donor 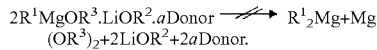 $R^1_2Mg+Mg(OR^3)_2+2LiOR^2+2a$Donor.

Dialkyl magnesium-containing reagents with n=0 typically also show excellent solubility in hydrocarbons.

$R^1$ preferably is an alkyl group consisting of 1-8 C-atoms. $OR^2$ and $OR^3$ may independently represent:

a) tert-alkoxy,
b) sec-alkoxy,
c) primary alkoxy $OCH_2CHR^4R^5$, consisting of 3-12 C-atoms, wherein the alkoxy residue has a branch at position 2 relative to the O-function and $R^4$ as well as $R^5$ independently represent alkyl radicals having 1-8 C-atoms,
d) alkoxy, containing another alkoxy function, of the general formula $O(CHR^6)_bOR^7$ wherein $R^6$=H or an alkyl radical having 1-6 C-atoms, which is either linear or has a branch at position 3 or higher relative to the O-function, $R^7$ is a linear or branched alkyl radical having 2-12 C-atoms, and b is an integer from 1 to 4, and wherein the donor is a diamine or a triamine, wherein a preferably represents a value between 0.5 and 1.5.

The residue $R_1$ preferably is isopropyl (i-Pr), n-butyl (n-Bu), sec-butyl (s-Bu), tert-butyl (t-Bu), or n-hexyl (n-Hex). tert-butylate (OtBu), tert-Amylat (OtAm), and 2,3-dimethyl-pentane-3-olate ($OC(CH_3)Et(iPr)$) are particularly preferred as tert-alkoxides. Preferably, 2-ethyl hexanolate ($OCH_2CH(Et)Bu$) is used as the primary alkoxide $OCH_2CHR^4R^5$. A sec-alkoxide can for example be $OCH(CH_3)Hex$. $OCH_2CH_2OBu$, $OCH_2CH_2OCH_2CH(Et)Bu$, and $OCH(Me)CH_2OBu$ are preferred as alkoxide containing another alkoxy function. The diamine base is for example tetramethylethylenediamine (TMEDA). An exemplary triamine is bis(2-dimethylaminoethyl)methylamine (PMDETA).

It is particularly preferred that exchange reagents are present as solutions having a concentration of at least 0.5 mol/kg in relation to Mg in a hydrocarbon or hydrocarbon mixture, wherein the solutions contain 1 wt % or less of an ethereal solvent.

It is further preferred that the exchange reagent is present as a solution in hydrocarbons, wherein the hydrocarbons are selected from the groups consisting of: aromatics and aliphates. The solution according to the invention preferably just contains quantities of 0.001 to 0.5 wt % of an oxygen-containing donor solvent. Particularly preferred aromatic solvents are toluene, ethylbenzene, and xylols. Preferred aliphates are hexane, heptane, octane, cyclohexane, methylcyclohexane, and commercially available petroleum ether mixtures.

The hydrocarbon-soluble reagents according to the invention for exchanging halogen or thiolate functions for magnesium of the general formula $R^1MgR^1_{1-n}(OR^3)_n.LiOR^2.(1-n)LiOR^3.a$Donor are used for exchange reactions with halogenated aromatics or heteroaromatics of the general formulas Hal-Ar and Hal-HetAr as well as thiolates of the general formulas $R^8S$—Ar and $R^8S$-HetAr according to the following reaction equations:

for n=1:

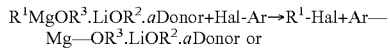

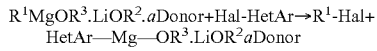

for n=0:

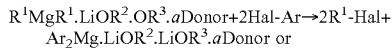

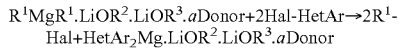

The same equations apply analogously to thiolate-functionalized substrates (in this case, replace Hal with $SR^8$).

The halogenated or thiolate-functionalized aromatics or heteroaromatics can have one or several functional groups, selected from the group consisting of: F, Cl, Br, CN, $CO_2R$, OR, OH, $NR_2$, NHR, $NH_2$, $PR_2$, $P(O)R_2$, $CONR_2$, CONHR, SR, SH, $CF_3$, $NO_2$.

In general, exchange reagents with n=1 are used for exchanging Br, I, or $SR^8$ groups, while the more reactive dialkyl magnesium-based reagents with n=0 can also be used for the magnesation of chlorine functions in aromatics or heteroaromatics. Chloroaromatics and chloro-heteroaromatics which are particularly easily accessible to magnesation have at least one alkoxy function in a position adjacent to chlorine. Examples include: 2-Chloroanisole; 1,2-chloromethoxynaphthalene; 2,3-chloromethoxynaphthalene; 1,5-dichloro-2-methoxy-4,6-dimethylbenzene, wherein magnesation is the exchange of the halogen or thiolate substituents on the halogenated or thiolate-functionalized aromatics or heteroaromatics.

It is particularly preferred that the hydrocarbon-soluble halogen/magnesium exchange reagents are used for exchange reactions with electron-rich halogenated aromatics and heteroaromatics of the general formulas Hal-At or Hal-HetAr, respectively.

Figure 2:
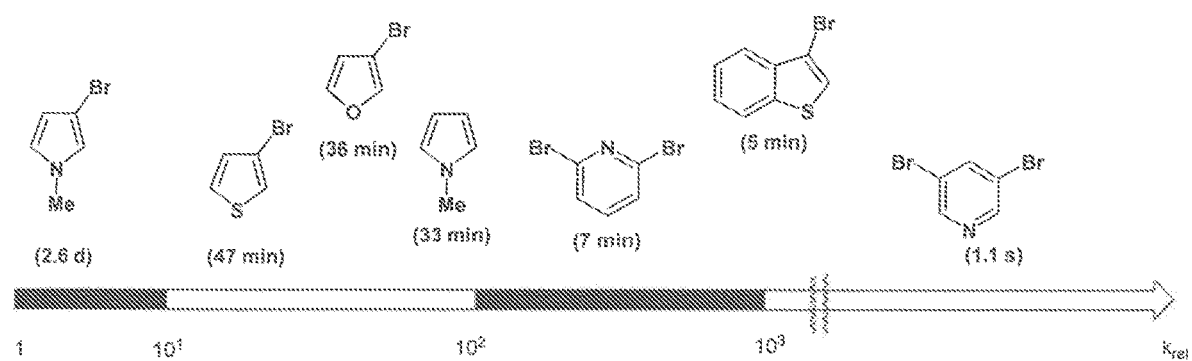
FIG. 2 depicts relative reactivities of heteroaryl bromides with i-PrMgCl.LiCl in THF solution at 0° C.

Electron-rich aromatics and heteroaromatics are attacked incompletely or very slowly only by the exchange reagents in THF solution known so far (L. Shi, Y. Chu, P. Knochel, H. Mayr, J. Org. Chem. 2009, 74, 2760; L. Shi, Y. Chu, P. Knochel, H. Mayr, Org. Lett. 2009, 11, 3502). In this connection, please reference FIG. 1 and FIG. 2.

Reaction times >1h are disadvantageous and prohibitive for practical applications. Electron-rich aromatics include such compounds that comprise inductively electron-donating groups (e.g. alkyl groups, phenyl groups) or mesomerically electron-donating groups (e.g. —$NR_2$, —NHR, $NH_2$, —OH, —OR, —NHC(O)—R and the like). The electron-rich heteroaromatics include, for example, five-membered ring compounds, such as pyrroles, furans, thiophenes, oxazoles, isoxazoles, thiazoles, isothiazoles, imidazoles, benzimidazoles, triazoles, indazoles, indoles, and the like.

Particularly preferred examples are the halogenated aromatics or heteroaromatics selected from the group consisting of: bromobenzene, bromotoluenes, bromoanisoles, bromo-N,N-dimethylanilines, 1-bromo-3,5-dimethoxybenzene, bromonaphthalenes, bromophenanthrenes, bromothiophenes, bromopyridines, bromobenzothiophenes, bromobenzofurans, 1,2-dibromocyclopent-1-ene, 2-chloroanisole, 1,2-chloromethoxynaphthalene, 2,3-chloromethoxynaphthalene, 1,5-dichloro-2-methoxy-4,6-dimethylbenzene.

The exchange reagents according to the invention are preferably also used for the thiolate/magnesium exchange of sulfur-functionalized, nitrogen-containing heteroaromatics. Examples include: Tert-butyl 2-(methylthio)piperidine-1-carboxylate, tert-butyl 2-(phenylthio)piperidine-1-carboxylate, tert-butyl 4-methyl-2-(phenylthio)piperidine-1-carboxylate, tert-butyl 2-((4-methoxyphenyl)thio)piperidine-1-carboxylate, tert-butyl 2-((4-fluorophenyl)thio)piperidine-1-carboxylate, tert-butyl 2-(phenylthio)pyrrolidine-1-carboxylate, 2-(phenylthio)pyridine.

It was surprisingly found that the exchange reagents according to the invention dissolved in toluene, for example the 4-bromoanisole used as test system, are capable of virtually complete metalation within 15 minutes (min) at room temperature, while the exchange reagents in THF known from document EP1582524B1 do not show a noteworthy reaction. The GC yields are determined after reaction with the electrophile water ($H_2O$):

Table 1: Bromium/magnesium exchange reactions on 4-bromoanisole using exchange reagents according to prior art (No. 1-12) and s-BuMgOCH$_2$CH(Et)Bu.LiOCH$_2$CH(Et)Bu in toluene according to the invention (No. 13-14)

TABLE 1

Bromium/magnesium exchange reactions on 4-bromoanisole using exchange reagents according to prior art (No. 1-12) and s-BuMgOCH$_2$CH(Et)Bu•LiOCH$_2$CH(Et)Bu in toluene according to the invention (No. 13-14)

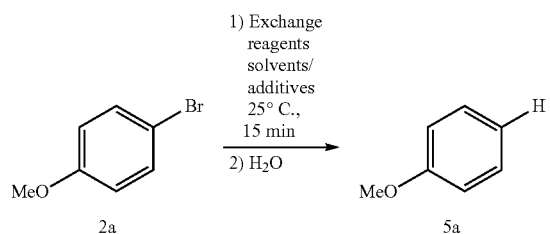 [SMILES: COc1ccc(Br)cc1 ; COc1ccccc1]

| No. | Exchange reagent | Solvent | TMEDA (equiv.) | GC yield (%) |
|---|---|---|---|---|
| 1 | i-PrMgCl•LiCl in THF (1.2 equiv.) | THF | 0 | 0.8 |
| 2 | i-PrMgCl•LiCl in THF (1.2 equiv.) | THF | 1.2 | 1.7 |
| 3 | i-PrMgCl•LiCl in toluene (1.2 equiv.) | toluene | 0 | 0 |
| 4 | i-PrMgCl•LiCl in toluene (1.2 equiv.) | toluene | 1.2 | 0 |
| 5 | s-Bu$_2$Mg•2 LiCl in THF (0.6 equiv.) | THF | 0 | 13. |
| 6 | s-Bu$_2$Mg•2 LiCl in THF (0.6 equiv.) | THF | 1.2 | 13. |
| 7 | s-Bu$_2$Mg•2 LiCl in toluene (0.6 equiv.) | toluene | 0 | 0 |
| 8 | s-Bu$_2$Mg•2 LiCl in toluene (0.6 equiv.) | toluene | 1.2 | 0 |
| 9 | s-BuMgCl•LiCl in THF (1.2 equiv.) | THF | 0 | 2 |
| 10 | s-BuMgCl•LiCl in THF (1.2 equiv.) | THF | 1.2 | 3 |
| 11 | s-BuMgCl•LiCl in toluene (1.2 equiv.) | toluene | 0 | 0 |
| 12 | s-BuMgCl•LiCl in toluene (1.2 equiv.) | toluene | 1.2 | 0 |
| 13 | s-BuMgOCH$_2$CH(Et)Bu• LiOCH$_2$CH(Et)Bu in toluene (1.2 equiv.) | toluene | 0 | 85 |
| 14 | s-BuMgOCH$_2$CH(Et)Bu• LiOCH$_2$CH(Et)Bu in toluene (1.2 equiv.) | toluene | 1.2 | 99 |

Various hydrocarbon-soluble exchange reagents were examined. Products with primary and secondary alcohol residues showed similar reactions to 4-bromoanisole, whereas products with tertiary alcohols showed a somewhat slower reaction behavior. An exception is 5-nonanolate (—OCHBu$_2$), which apparently did not lead to a reaction under the mild reaction conditions due to steric hindrance (Table 2).

TABLE 2

Exchange reactions to 4-bromoanisole using various exchange reagents (variation of the alcohol residue)

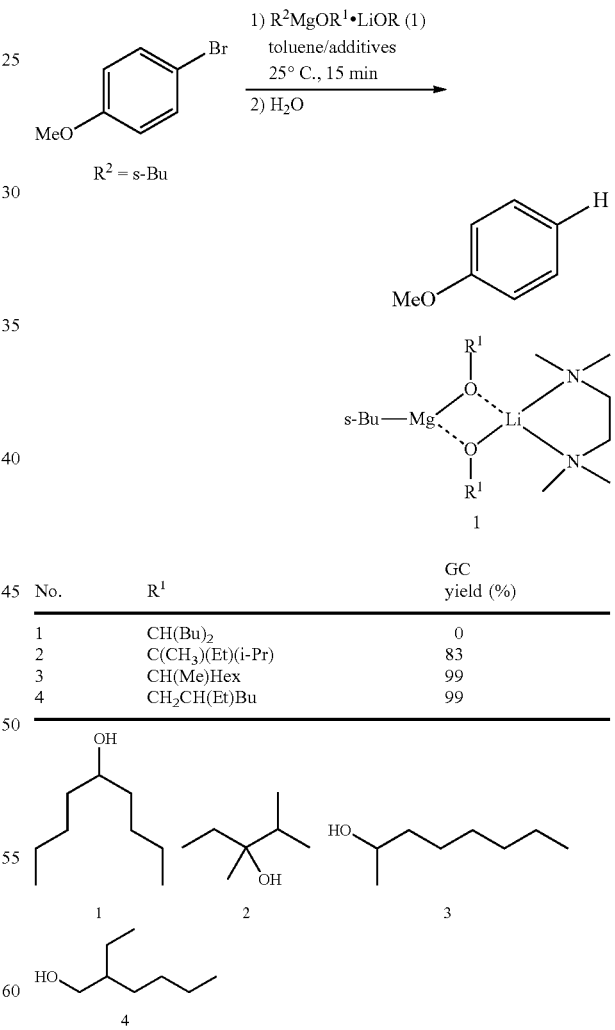

| No. | R$^1$ | GC yield (%) |
|---|---|---|
| 1 | CH(Bu)$_2$ | 0 |
| 2 | C(CH$_3$)(Et)(i-Pr) | 83 |
| 3 | CH(Me)Hex | 99 |
| 4 | CH$_2$CH(Et)Bu | 99 | sec-BuMgOCH$_2$CH(Et)Bu.LiOCH$_2$CH(Et)Bu, which was tested for metalation of various functionalized bromobenzenes, proved to be a particularly advantageous exchange reagent (Table 3).

TABLE 3

Halogen-magnesium exchange on aryl compounds $$\text{2} \xrightarrow[\text{toluene/TMEDA, 25°C}]{\text{1) s-BuMgOCH}_2\text{CH(Et)Bu} \cdot \text{LiOCH}_2\text{CH(Et)Bu (1a)}} \text{3 (ArMgOR}\cdot\text{LiOR}\cdot\text{TMEDA)} \xrightarrow{\text{2) E—X}} \text{5}$$

| No. | Educt | E (equiv.) | Time (min) | Product/yield[a] |
|---|---|---|---|---|
| 1 | 4-MeO-C6H4-Br (2a) | H2O, a (1.2) | 15 | PhOMe, 5a, 96% |
| 2 | 2a | I2, b (1.2) | 15 | 4-MeO-C6H4-I, 5b, 70% |
| 3 | 2a | MeSSMe, c (1.2) | 15 | 4-MeO-C6H4-SMe, 5c, 93% |
| 4 | 2a | 3-pentanone, d (1.2) | 15 | 4-MeO-C6H4-C(Et)2OH, 5d, 80% |
| 5 | 2a | MeC(O)N(OMe)Me (Weinreb amide), e (1.2) | 15 | 4-MeO-C6H4-C(O)Me, 5e, 92% |
| 6 | 2a | PhC(O)-morpholine, f (1.2) | 15 | 4-MeO-C6H4-C(O)Ph, 5f, 70% |
| 7 | 3-MeO-C6H4-Br (2b) | I2, a (1.2) | 15 | 3-MeO-C6H4-I, 5g, 65% |

TABLE 3-continued
Halogen-magnesium exchange on aryl compounds
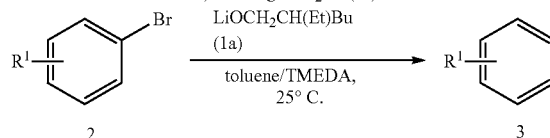
| No. | Educt | E (equiv.) | Time (min) | Product/yield[a] |
|---|---|---|---|---|
| 8 | 2b | MeSSMe<br>c (1.2) | 15 | 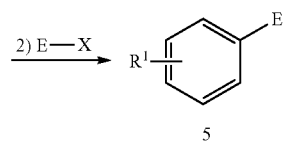<br>5h, 96% |
| 9 | 2b | 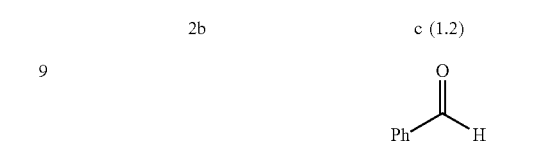<br>g (1.2) | 15 | <br>5i, 99% |
| 10 | <br>2c | 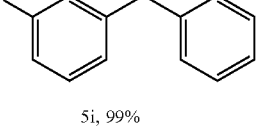<br>e (1.2) | 15 | 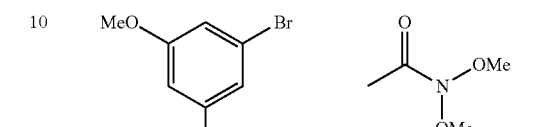<br>5j, 89% |
| 11 | 2c | 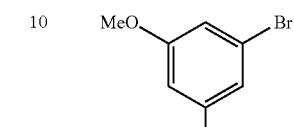<br>f (1.2) | 15 | 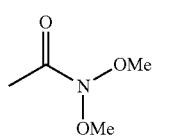<br>5k, 67% |
| 12 | 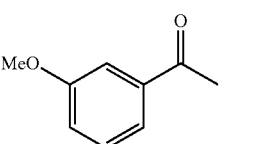<br>2d | MeSSMe<br>c (1.2) | 60 | 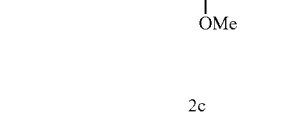<br>5l, 84% |
| 13. | 2d | <br>g (1.2) | 60 | 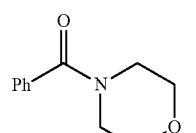<br>5m, 80% |
| 14 | 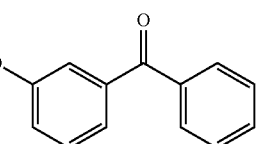 | MeSSMe | 90 |  |

TABLE 3-continued

Halogen-magnesium exchange on aryl compounds $$2 \xrightarrow[\text{toluene/TMEDA, 25°C}]{\text{1) s-BuMgOCH}_2\text{CH(Et)Bu} \cdot \text{LiOCH}_2\text{CH(Et)Bu (1a)}} 3 \xrightarrow{\text{2) E—X}} 5$$

| No. | Educt | E (equiv.) | Time (min) | Product/yield[a] |
|---|---|---|---|---|
| 15 | 2e (4-Me₂N-C₆H₄-Br) | c (1.2) PhC(O)H | 240 | 5n, 76% (4-Me₂N-C₆H₄-C(O)-Ph) |

This reagent was also tested for Mg/Br exchange on heteroaryl compounds (Table 4):

TABLE 4

Halogen-magnesium exchange on heteroaryl compounds $$6 \xrightarrow[\text{toluene/TMEDA}]{\text{1) s-BuMgOCH}_2\text{CH(Et)Bu} \cdot \text{LiOCH}_2\text{CH(Et)Bu (1a)}} 7 \xrightarrow{\text{2) E—X}} 8$$

Z = O, S
X = Br, Cl

| No. | Educt | E (equiv.) | Time (min) | Product/yield[a] |
|---|---|---|---|---|
| 1 | 6a (5-Br-benzofuran) | PhC(O)-morpholine (1.2) | 10 | 8a; 70%[b] (5-benzoyl-benzofuran) |
|  | 6a | (1.2) |  | 8a; 70%[b] |
| 2 |  |  | 10 | 8B; 74%[b] (furan-2-yl(benzofuran-5-yl)methanol) |
|  | 6a | (1.2) |  | 8b; 74%[b] |

TABLE 4-continued

Halogen-magnesium exchange on heteroaryl compounds

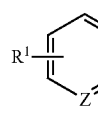

Z = O, S
X = Br, Cl

| No. | Educt | E (equiv.) | Time (min) | Product/yield[a] |
|---|---|---|---|---|
| 3 | 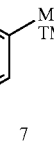<br>6b | 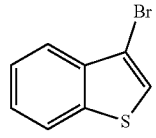<br>(1.2) | 10 | 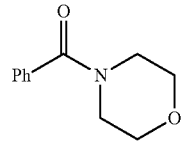<br>8c; 65%[c] |
|  | 6b | (1.2) |  | 8c; 65%[c] |
| 4 | 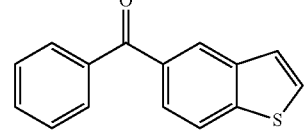<br>6c | 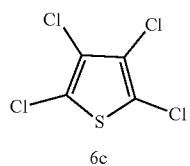<br>a (2.6) | 240 | 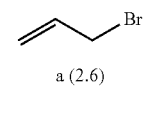<br>8d, 60%[b] |
|  | 6c | a (2.6) |  | 8d, 60%[b] |

[a]Yield of the analytically pure product.
[b]The reactions were performed at 25° C.
[c]The reaction was performed at −10° C.

Figure 3:
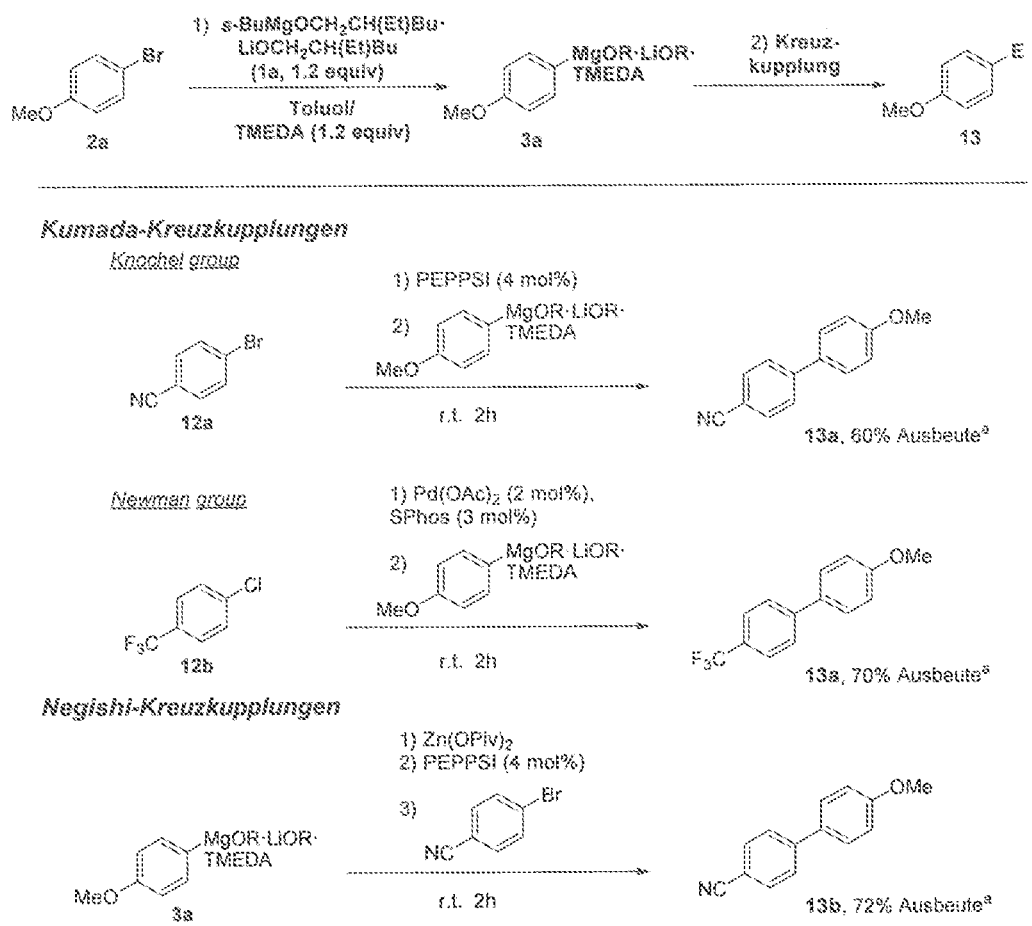
FIG. 3 depicts results of using metalated aromatics for cross-coupling reactions.

FIG. 3 shows results of using metalated aromatics for cross-coupling reactions.

Figure 4:
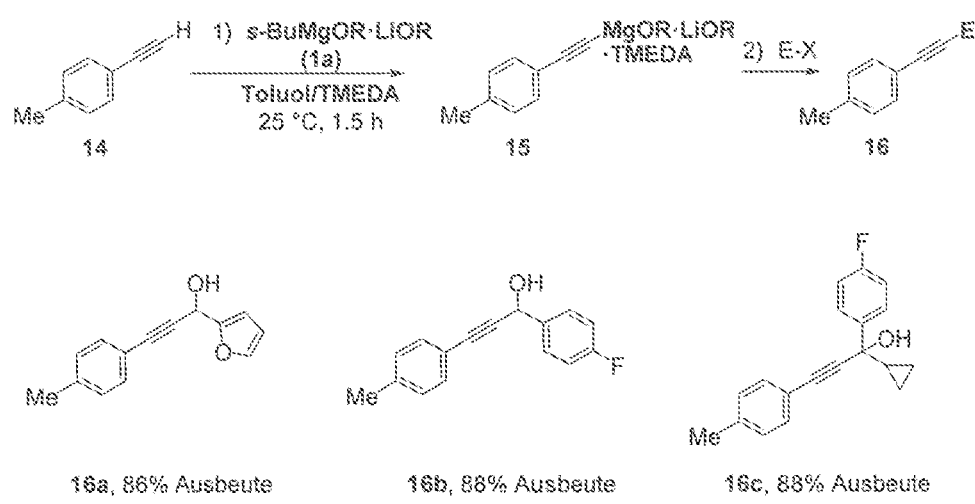
FIG. 4 depicts use of HC-soluble exchange reagents for deprotonating alkines.

Furthermore, the hydrocarbon-soluble halogen/magnesium exchange reagents can be used for deprotonating terminal alkines. Organic intermediates, preferably carbinols, can be obtained by subsequently reacting with electrophiles, for example carbonyl compounds. Ethinyl toluene was used as test system for deprotonation (FIG. 4):

The exchange reagents according to the invention are obtained using the following three alternative methods, in that 1) a dialkoxy magnesium compound $R^2O$—Mg—$OR^3$ with (n+1) equivalents is reacted with an alkyl lithium compound $R^1Li$ in a hydrocarbon-containing solvent or solvent mixture, wherein $R^1$ preferably is an alkyl group consisting of 1-8 C-atoms. n preferably assumes the values 0 or 1, and $OR^2$ and $OR^3$ may independently represent:
   a) tert-alkoxy,
   b) sec-alkoxy,
   c) primary alkoxy $OCH_2CHR^4R^5$, consisting of 3-12 C-atoms, wherein the alkoxy residue has a branch at position 2 relative to the O-function and $R^4$ as well as $R^5$ independently represent alkyl radicals having 1-8 C-atoms,
   d) alkoxy, containing another alkoxy function, of the general formula $O(CHR^6)_bOR^7$ wherein $R^6$=H or an alkyl radical having 1-6 C-atoms, which is either linear or has a branch at position 3 or higher relative to the O-function, $R^7$ is a linear or branched alkyl radical having 2-12 C-atoms, and b is an integer from 1 to 4, $R^2O$—Mg—$OR^3$+(n+1)$R^1$—Li→$R^1MgR^1_{1-n}(OR^3)$. $LiOR^2.(1-n)LiOR^3$ or 2) a dialkoxy magnesium compound $R^1$—Mg—$R^9$ is reacted for n=1 with an equivalent of an alcohol $R^3OH$ and one equivalent of a lithium alkoxide compound $R^2OLi$ in a hydrocarbon-containing solvent or solvent mixture, or for n=0 a total of two equivalents of lithium alkoxide compounds $R^2OLi$ and/or $R^3OLi$ are added, wherein $R^9$=alkyl consisting of 1-8 C-atoms, same as or different from $R^1$, otherwise the same description of the substituents $R^1$ to $R^8$ applies as described above:
   1a. $R^1$—Mg—$R^9$+$R^3$—OH→$R^1$—Mg—$OR^3$+$HR^9$
   1b. $R^1$—Mg—$OR^3$+$LiOR^2$→$R^1$—Mg—$OR^3.LiOR^2$
   2. $R^1$—Mg—$R^9$+$LiOR^2$+$LiOR^3$→$R^1$—Mg—$R^9.LiOR^2.LiOR^3$ or 3) a dialkoxy magnesium compound $R^1$—Mg—$R^9$ is reacted with one equivalent of a dialkoxy magnesium compound $R^5O$—Mg—$OR^3$ in a hydrocarbon-containing solvent or solvent mixture, and 0.5 to 1.5 equivalents of a lithium alkoxide compound $R^2OLi$ are added to this reaction mixture, likewise with the definition of the substituents $R^2$ to $R^8$ as described above.

1. $R^1MgR^9 + R^5O-Mg-OR^3 \rightarrow 2[(R^3O)_{0.5}(R^5O)_{0.5}]Mg[R^1_{0.5}R^9_{0.5}]$
2. $[(R^3O)_{0.5}(R^5O)_{0.5}]Mg[R^1_{0.5}R^9_{0.5}] + LiOR^2 \rightarrow [(R^3O)_{0.5}(R^5O)_{0.5}]Mg[R^1_{0.5}R^9_{0.5}].LiOR^2$ The following substituent definitions apply:

R and R* a substituted or non-substituted $C_4$-$C_{24}$ aryl or $C_3$-$C_{24}$ heteroaryl containing one or several heteroatoms such as B, O, N, S, Se, P, F, Cl, Br, I, or Si; a linear or branched, substituted or non-substituted $C_2$-$C_{20}$ alkyl, $C_2$-$C_{20}$ alkenyl, or $C_2$-$C_{20}$ alkinyl; or substituted or non-substituted $C_3$-$C_{20}$ cycloalkyl $R^1$, $R^4$, $R^5$, $R^9$ an alkyl group consisting of 1-8 C-atoms $R^2$, $R^3$ contain an alkoxy substituent $OR^4$ $R^6$ is H or an alkyl radical having 1-6 C-atoms, which is either linear or has a branch at position 3 or higher relative to the O function $R^7$ a linear or branched alkyl radical having 2-12 C-atoms $R^8$ alkyl or aryl, preferably phenyl $OR^2$ and $OR^3$ same or different and primary, secondary, or tertiary alkoxy groups containing 3 to 18 carbon atoms Hal-Ar halogenated aromatics Hal-HetAr halogenated heteroaromatics $R^8$S—Ar aryl thiolate $R^8$S-HetAr heteroaryl thiolate The method can be improved in that equivalents of a donor are added to the reaction mixture from synthesis a in relation to Mg, wherein the donor is a diamine or a triamine and a has a value of 0 to 2, preferably 0.5 to 1.5. Advantageously, hydrocarbon-containing solvents are used in all methods.

The metalated intermediates Ar—Mg—$OR^3$.$LiOR^2$.aDonor, HetAr—Mg—$OR^3$.$LiOR^2$.aDonor, $Ar_2$Mg $LiOR^2$.$LiOR^3$.aDonor as well as HetAr$_2$Mg.$LiOR^2$.$LiOR^3$.aDonor are preferably used for CC or CN coupling reactions (Kumada type cross-couplings, mostly Pd-catalyzed) or for addition reactions by reaction with electrophiles. Suitable electrophiles are all compounds which react with carbanionic reaction centers, for example carbonyl compounds (aldehydes, ketones, carboxylic acid esters, carboxylic acid amides), nitriles, imines, halogens, halogen compounds, disulfides, water, and others.

The invention is explained in greater detail below with reference to exemplary embodiments.

General Information

All reactions were performed in an argon atmosphere in baked-out glassware. Syringes, which were used for the transfer of anhydrous solvents or reagents, were first flushed with argon. Toluene and THF were continuously refluxed and used freshly distilled over sodium benzophenone in a nitrogen atmosphere. The solvents were stored dry using a molecular sieve. TMEDA and 2-ethylhexanol were freshly distilled using calcium hydride. The yields refer to the isolated compounds, which are estimated to be >95% pure, determined by $^1$H-NMR (25° C.) and gas chromatography (GC). The compounds were purified by means of column chromatography, wherein silica gel was used ($SiO_2$ 0.040-0.063 mm, 230-400 mesh ASTM).

NMR spectra were measured in $CDCl_3$, and chemical compounds were measured in parts per million (ppm). The abbreviations for signal couplings are as follows: s, singlet; d, doublet; t, triplet; q, quartet; m, multiplet; br, broad. Mass spectra and high resolution mass spectra (HRMS) were determined using electron ionization (EI) GC spectra were measured using machines of the Hewlett Packard type, 6890 or 5890 series (Hewlett Packard, 5% phenylmethyl polysiloxane; length: 10 m, diameter: 0.25 mm; film thickness: 0.25 µm). All reagents were purchased from commercially available sources. Magnesium-2-ethylhexanoate was received from Albemarle (Frankfurt/Hoechst).

EXAMPLES

Example 1: Preparation of sec-BuMgOCH$_2$CH(Et)Bu.LiOCH$_2$CH(Et)Bu from magnesium bis(2-ethylhexanolate) and sec-BuLi A dry Schlenk flask, which was filled with argon and equipped with a magnetic stirrer bar and a septum, was filled with Mg[OCH$_2$CH(Et)Bu]$_2$ (0.85 M in heptane, 15.0 mL, 12.8 mmol), and the reaction mixture was cooled to 0° C. Then s-BuLi (1.21 M in hexane, 10.6 mL, 12.8 mmol) was added drop by drop. After the addition was complete, the reaction mixture was brought to 25° C. and the reaction solution was stirred for 2 hours. A slightly yellowish solution was created in the process. Then the solvent was evaporated off in a vacuum, resulting in a light yellow foam. Freshly distilled toluene (approx. 9 mL) was added under constant stirring at 0° C. The sec-BuMgOCH$_2$CH(Et)Bu.LiOCH$_2$CH(Et)Bu prepared in this way was iodometrically titrated at 0° C. The concentration of the resulting clear solution was equivalent to molarity of 0.80-1.3 M.

Example 2: Preparation of sec-BuMgOCH$_2$CH(Et)Bu.LiOCH$_2$CH(Et)Bu from dibutyl magnesium, bis(2-ethylhexanol), and sec-BuLi A dry Schlenk flask, which was filled with argon and equipped with a magnetic stirrer bar and a septum, was filled with n-Bu$_2$Mg (0.66 M in hexane, 15.0 mL, 9.9 mmol). Then 2-ethylhexanol (3.1 mL, 19.8 mmol) was slowly added by dripping at 0° C. under ice cooling. A gelatinous compound was created while releasing heat. This compound was then mixed at 0° C. with s-BuLi (1.21 M in hexane, 8.18 mL, 9.9 mmol). After the addition was complete, the reaction mixture was brought to 25° C. and the reaction solution was stirred for 2 hours. The gelatinous compound dissolved in the process, and a slightly yellowish solution was created. Then the solvent was evaporated off in a vacuum, resulting in a light yellow foam. Freshly distilled toluene (approx. 1 mL) was added under constant stirring at 0° C.

Example 3: Preparation of n-BuMgOCH$_2$CH(Et)Bu.LiOCH$_2$CH(Et)Bu

A dry Schlenk flask, filled with argon and equipped with a magnetic stirrer bar and a septum, was filled with Mg[OCH$_2$CH(Et)Bu]2 (0.85 M in heptane, 15.0 mL, 12.8 mmol), and the reaction mixture was cooled to 0° C. Then n-BuLi (2.1 M in hexane, 6.1 mL, 12.8 mmol) was added drop by drop. After the addition was complete, the reaction mixture was brought to 15° C. and the reaction solution was stirred for 2 hours. A slightly yellowish solution was created in the process. Then the solvent is evaporated off in a vacuum, resulting in a light yellow foam. Freshly distilled toluene (approx. 9 mL) was added under constant stirring at 0° C.

Example 4: Preparation of sec-Bu$_2$Mg.2 LiOCH$_2$CH(Et)Bu.PMDTA from dibutyl magnesium, bis(2-ethylhexanol), and sec-BuLi in toluene A dry Schlenk flask, which was filled with argon and equipped with a magnetic stirrer bar and a septum, was filled with n-Bu$_2$Mg (0.66 M in hexane, 15.0 mL, 9.9 mmol). Then 2-ethylhexanol (3.1 mL, 19.8 mmol) was slowly added by dripping at 0° C. under ice cooling. A gelatinous compound was created while releasing heat. This compound was then mixed at 0° C. with s-BuLi (1.21 M in hexane, 16.36 mL, 19.8 mmol). After the addition was complete, the reaction mixture was brought to 25° C. and the reaction solution was stirred for 2 hours. The gelatinous compound dissolved in the process, and a slightly yellowish solution was created. Then the solvent was evaporated off in a vacuum, resulting in a light yellow foam. Freshly distilled toluene (approx. 1 mL) was added under constant stirring at 0° C.

Example 5: Preparation of sec-Bu$_2$Mg.2 LiOCH$_2$CH(Et)Bu from magnesium bis(2-ethylhexanolate) and sec-BuLi A dry Schlenk flask, which was filled with argon and equipped with a magnetic stirrer bar and a septum, was filled with Mg[OCH$_2$CH(Et)Bu]$_2$ (0.85 M in heptane, 15.0 mL, 12.8 mmol), and the reaction mixture was cooled to 0° C. Then sec-BuLi (1.21 M in hexane, 21.2 mL, 25.6 mmol) was added drop by drop. After the addition was complete, the reaction mixture was brought to 25° C. and the reaction solution was stirred for 2 hours. A slightly yellowish solution was created in the process. Then the solvent was evaporated off in a vacuum, resulting in a light yellow foam. Freshly distilled toluene (approx. 9 mL) was added under constant stirring at 0° C. The s-BuMg$_2$.2LiOCH$_2$CH(Et)Bu was then iodometrically titrated at 0° C. The concentration of the resulting clear solution was equivalent to molarity of 0.60-0.85 M.

Example 6: Typical Procedure for the Preparation of Aryl and Heteroaryl Magnesium Alkoxide Compounds by a Bromium-Magnesium Exchange A dry flask filled with argon, equipped with a magnetic stirrer bar and a septum, is filled with the respective aryl or heteroaryl bromide (1.0 eq.) and dissolved in dry toluene (0.5 M solution) and TMEDA (1.2 eq.). The resulting solution is stirred at the respective specified temperature, and sec-BuMgOCH$_2$CH(Et)Bu.LiOCH$_2$CH(Et)Bu (1.2 eq.) is added by dripping. The end of the bromium-magnesium exchange is verified by GC analysis of aliquots quenched with water, wherein tetradecane is used as internal standard. Then the aryl or heteroaryl magnesium alkoxide compounds are reacted with electrophiles under the specified conditions. After the reactions are complete, the reaction mixtures are quenched with saturated aqueous NH$_4$Cl solution and extracted with EtOAc (3×20 ml). The combined organic phases are dried over Na$_2$SO$_4$, filtrated, and concentrated.

$^{13}$C-NMR (101 MHz, CDCl$_3$): δ/ppm=153.8, 151.0, 143.2, 133.2, 128.2, 127.3, 126.6, 114.1, 112.8, 111.9, 72.3, 56.0, 55.7.

MS (EI, 70 eV): m/z (%)=244 (100), 226 (11), 167 (13), 165 (15), 139 (45), 105 (30), 91 (14), 79 (12), 77 (28), 43 (37).

HRMS (EI): m/z calc. for [C$_{15}$H$_{16}$O$_3$]: 244.1099; found: 244.1095.

IR (Diamond-ATR, neat): ṽ/cm$^{-1}$=2938, 2834, 1591, 1492, 1452, 1276, 1212, 1177, 1037, 831.

Example 9: Typical Procedure for the Preparation of Heteroaryl Magnesium Alkoxide Compounds by a Thiolate-Magnesium Exchange A dry flask filled with argon, equipped with a magnetic stirrer bar and a septum, is filled with the respective thiolate-functionalized heteroarene (1.0 eq.) and dissolved in dry toluene (0.5 M solution) and mixed with approx. 3 eq. TMEDA. The resulting solution is stirred at room temperature, and sec-BuMgOCH$_2$CH(Et)Bu.LiOCH$_2$CH(Et)Bu (3.0 eq.) is added by dripping (0.05 mL/min). The end of the thiolate-magnesium exchange is verified by GC analysis of aliquots quenched with water, wherein tetradecane is used as internal standard. Subsequently, the heteroaryl magnesium alkoxide compounds are reacted with electrophiles under the specified conditions. After the reaction is complete, the reaction mixtures are quenched with saturated aqueous NH$_4$Cl solution and extracted with Et$_2$O (3×20 mL). The combined organic phases are dried over Na$_2$SO$_4$, filtrated, and concentrated.

Example 10: Preparation of tert-butyl 2-allyl-4-methylpiperidine-1-carboxylate

According to the procedure specified in Example 9, sec-BuMgOCH$_2$CH(Et)Bu.LiOCH$_2$CH(Et)Bu (1.10 M in Toluol, 0.82 mL, 0.9 mmol 3.0 eq.) was added by dripping (0.05 mL/min) to a mixture of tert-butyl 2-(methylthio)piperidine-1-carboxylate (92 mg, 0.30 mmol), TMEDA (0.134 mL, 0.9 mmol), and toluene (0.6 mL) at 25° C. After 4 hours, allyl bromide (78 μL, 0.9 mmol, 3.0 eq.) was added at 0° C., the reaction mixture was cooled to −40° C. and mixed with CuCN. 2 LiCl solution (1.0 M in THF, 0.09 mL, 0.09 mmol, 0.3 eq.), and then the mixture was stirred for another 14 hours at 25° C. The crude product was purified using column chromatography (silica gel, i-hexane/diethylether 95:5) and yielded the title compound as a colorless oil (59 mg, 0.25 mmol, 83%).

$^1$H-NMR (599 MHz, CDCl$_3$): δ/ppm=5.77 (ddt, J=17.2, 10.2, 7.2 Hz, 1H), 5.08-4.97 (m, 2H), 3.85 (tt, J=8.3, 6.3 Hz, 1H), 3.73 (ddd, J=13.9, 7.3, 3.2 Hz, 1H), 3.01 (ddd, J=13.9, 10.3, 5.9 Hz, 1H), 2.40 (dddt, J=14.2, 7.1, 5.9, 1.4 Hz, 1H), 2.24 (dtt, J=13.5, 7.6, 1.1 Hz, 1H), 1.87 (ddtd, J=13.3, 10.3, 7.2, 1.2 Hz, 1H), 1.73-1.68 (m, 1H), 1.68-1.62 (m, 1H), 1.45 (s, 8H), 1.20-1.12 (m, 1H), 1.12-1.06 (m, 1H), 0.98 (d, J=6.8 Hz, 3H).

$^{13}$C-NMR (101 MHz, CDCl$_3$): δ/ppm=155.4, 135.4, 116.7, 79.0, 53.0, 39.0, 37.4, 34.9, 31.1, 28.4, 26.1, 21.5.

MS (EI, 70 eV): m/z (%)=166 (3), 143 (8), 142 (100), 98 (46), 57 (3), 56 (5).

HRMS (EI): m/z calc. for [C$_{10}$H$_{16}$ON]: 166.1232; found: 166.1225.

IR (Diamond-ATR, neat): ṽ/cm$^{-1}$=2976, 2928, 2872, 1688, 1642, 1478, 1456, 1408, 1392, 1364, 1350, 1332, 1304, 1278, 1246, 1178, 1148, 1094, 1070, 992, 912, 866, 770.

Example 11: Typical Procedure for the Preparation of Alkinyl Magnesium Alkoxide Compounds by Deprotonation A dry flask filled with argon, equipped with a magnetic stirrer bar and a septum, is filled with the respective alkine (1.0 eq.) and dissolved in dry toluene (0.5 M solution) and TMEDA (1.2 eq.). The resulting solution is stirred at the respective specified temperature, and sec-BuMgOCH$_2$CH(Et)Bu.LiOCH$_2$CH(Et)Bu (1.2 eq.) is added by dripping. The end of the deprotonation is verified by GC analysis of aliquots quenched with water, wherein tetradecane is used as internal standard. Then the alkinyl magnesium alkoxide compounds are reacted with electrophiles under the specified conditions (see FIG. 4). After the reaction is complete, the reaction mixtures are quenched with saturated aqueous NH₄Cl solution and extracted with EtOAc (3×20 mL). The combined organic phases are dried over Na₂SO₄, filtrated, and concentrated.

Example 12: Preparation of 4-iodoanisole

According to the procedure specified in Example 7, sec-BuMgOCH₂CH(Et)Bu.LiOCH₂CH(Et)Bu (0.80 M in toluene, 0.75 mL, 0.6 mmol, 1.2 eq.) was added by dripping to a mixture of 4-bromoanisole (0.06 mL, 0.50 mmol), TMEDA (0.09 mL, 0.6 mmol), and toluene (1 mL) at 25° C. After 15 minutes, iodine (152 mg in 1 mL THF, 0.6 mmol, 1.2 eq.) was added and the reaction mixture was stirred for another 30 minutes at 25° C. The crude product was purified using column chromatography (silica gel, i-hexane/ethylacetate 9:1) and yielded the title compound as a white solid substance (81 mg, 0.35 mmol, 70%).

¹H-NMR (400 MHz, CDCl₃): δ/ppm=7.63-7.49 (d, 2H), 6.76-6.61 (d, 2H), 3.78 (s, 3H).

¹³C-NMR (101 MHz, CDCl₃): δ/ppm=159.6, 138.3, 116.5, 82.8, 55.5.

MS (EI, 70 eV): m/z (%)=234 (100), 191 (15), 92 (64).

HRMS (EI): m/z calc. for [C₇H₇IO]: 233.9542; found: 233.9540.

IR (Diamond-ATR, neat): ˜V/cm⁻¹=3006, 2966, 2938, 2837, 1586, 1569, 1486, 1456, 1444, 1436, 1397, 1287, 1248, 1179, 1175, 1102, 1028, 999, 833, 829, 813.8

The invention claimed is:

1. Hydrocarbon-soluble exchange reagents of the general formula:

$R^1MgR^1_{1-n}(OR^3)_n \cdot LiOR^2 \cdot (1-n)LiOR^3 \cdot a\text{Donor}$ wherein $R^1$ is selected from the group consisting of isopropyl (i-Pr), n-butyl (n-Bu), sec-butyl (s-Bu), tert-butyl (t-Bu) and n-hexyl (n-Hex) and $OR^2$ and $OR^3$ are each independently selected from the group consisting of:
a) tert-alkoxy,
b) sec-alkoxy,
c) primary alkoxy $OCH_2CHR^4R^5$, having 3 to 12 carbon atoms, wherein the alkoxy residue has a branch at position 2 relative to the O-function and $R^4$ and $R^5$ independently represent alkyl radicals having 1 to 8 carbon atoms, and
d) alkoxy, containing another alkoxy function, of the general formula $O(CHR^6)_bOR^7$ wherein $R^6$=H or an alkyl radical having 1 to 6 carbon atoms, which is either linear or has a branch at position 3 or higher relative to the O-function, $R^7$ is a linear or branched alkyl radical having 2 to 12 carbon atoms, and b=an integer from 1 to 4;
wherein $R^2$ and/or $R^3$ contain an alkoxy substituent $OR^4$, a has a value of 0 to 2, n has a value from 0 to 1, and the Donor is an organic molecule containing at least 2 nitrogen atoms.

2. The hydrocarbon-soluble exchange reagents according to claim 1, characterized in that the donor is a diamine or a triamine, wherein a has a value between 0.5 and 1.5 and n has a value of 0 or 1.

3. The hydrocarbon-soluble exchange reagents according to claim 1, characterized in that the hydrocarbon-soluble exchange reagents are present as solutions having a concentration of at least 0.5 mol/kg in relation to Mg in a hydrocarbon or hydrocarbon mixture, wherein the solution contains 1 wt % or less of an ethereal solvent.

4. The hydrocarbon-soluble exchange reagents according to claim 1, characterized in that the hydrocarbons are selected from the group consisting of aromatics and aliphates.

5. The hydrocarbon-soluble exchange reagents according to claim 1, characterized in that $R^1$ is exchanged for the aromatic residue Ar or HetAr by reacting with electron-rich halogen aromatics (Hal-Ar), or halogen heteroaromatics (Hal-HetAr), wherein Hal=Cl, Br, or I, or aryl thiolates $R^8S$—Ar, or hetero aryl thiolates $R^8S$-HetAr, wherein $R^8$=alkyl, aryl, or phenyl.

6. A method for preparing the hydrocarbon-soluble exchange reagents according to claim 1, characterized in that a dialkoxy magnesium compound $R^2O$—Mg—$OR^3$ is reacted with (n+1) equivalents of an alkyl lithium compound $R^1Li$ in a hydrocarbon-containing solvent or solvent mixture, wherein: $R^1$ is selected from the group consisting of isopropyl (i-Pr), n-butyl (n-Bu), sec-butyl (s-Bu), tert-butyl (t-Bu) and n-hexyl (n-Hex),
n has a value of 1 or 0, and
$OR^2$ and $OR^3$ are each independently selected from the group consisting of:
a) tert-alkoxy,
b) sec-alkoxy,
c) primary alkoxy $OCH_2CHR^4R^5$ having 3 to 12 carbon atoms, wherein the alkoxy residue has a branch at position 2 relative to the O-function and $R^4$ and $R^5$ independently represent alkyl radicals having 1 to 8 carbon atoms, and
d) alkoxy residue, containing another alkoxy function, of the general formula $O(CHR^6)_bOR^7$ wherein $R^6$=H or an alkyl radical having 1 to 6 carbon atoms, which is either linear or has a branch at position 3 or higher relative to the O-function, $R^7$ is a linear or branched alkyl radical having 2 to 12 carbon atoms, and b is an integer from 1 to 4.

7. A method for preparing hydrocarbon-soluble exchange reagents according to claim 1, characterized in that a dialkyl magnesium compound $R^1$—Mg—$R^9$ is reacted, for n=1, with one equivalent alcohol $R^3OH$ and one equivalent of a lithium alkoxide compound $R^2OLi$, or, for n=0, with a total of two equivalents of the lithium alkoxide compounds $R^2OLi$ and/or $R^3OLi$ in a hydrocarbon-soluble solvent or solvent mixture, wherein:
$R^1$ is selected from the group consisting of isopropyl (i-Pr), n-butyl (n-Bu), sec-butyl (s-Bu), tert-butyl (t-Bu) and n-hexyl (n-Hex), and
$OR^2$ and $OR^3$ each are independently selected from the group consisting of:
a) tert-alkoxy,
b) sec-alkoxy,
c) primary alkoxy $OCH_2CHR^4R^5$, having 3 to 12 carbon atoms, wherein the alkoxy residue has a branch at position 2 relative to the O-function and $R^4$ and $R^5$ independently represent alkyl radicals having 1 to 8 carbon atoms,
d) alkoxy residue, containing another alkoxy function, of the general formula $O(CHR^6)_bOR^7$ wherein $R^6$=H or an alkyl radical having 1 to 6 carbon atoms, which is either linear or has a branch at position 3 or higher relative to the O-function, $R^7$ is a linear or branched alkyl radical having 2 to 12 carbon atoms, and b is an integer from 1 to 4, and
$R^9$ is any alkyl group having 1 to 8 carbon atoms and $R^9$ is either the same as, or different from, $R^1$.

8. A method for preparing hydrocarbon-soluble exchange reagents according to claim 1, characterized in that a dialkyl magnesium compound $R^1$—Mg—$R^9$ is reacted with one equivalent of a dialkoxy magnesium compound $R^5O$—Mg—$OR^3$ in a hydrocarbon-containing solvent or solvent mixture, and 0.5 to 1.5 equivalents of an alkyl lithium compound $R^2OLi$ are added to this reaction mixture, wherein:

$R^1$ is selected from the group consisting of isopropyl (i-Pr), n-butyl (n-Bu), sec-butyl (s-Bu), tert-butyl (t-Bu) and n-hexyl (n-Hex), and $OR^2$ and $OR^3$ each are independently selected from the group consisting of:
 a) tert-alkoxy,
 b) sec-alkoxy,
 c) primary alkoxy $OCH_2CHR^4R^5$, having 3 to 12 carbon atoms, wherein the alkoxy residue has a branch at position 2 relative to the O-function and $R^4$ and $R^5$ independently represent alkyl radicals having 1 to 8 carbon atoms, and
 d) alkoxy residue, containing another alkoxy function, of the general formula $O(CHR^6)_bOR^7$ wherein $R^6$=H or an alkyl radical having 1 to 6 carbon atoms, which is either linear or has a branch at position 3 or higher relative to the O-function, $R^7$ is a linear or branched alkyl radical having 2 to 12 carbon atoms, and b is an integer from 1 to 4.

9. The method for preparing hydrocarbon-soluble exchange reagents according to claim 6, characterized in that equivalents of a donor are added to the reaction mixture from synthesis a in relation to Mg, wherein the donor is a diamine or a triamine and a has a value of 0.5 to 1.5.

10. The method for preparing hydrocarbon-soluble exchange reagents according to claim 6, characterized in that only hydrocarbon-based solvents are used.

11. A process comprising reacting the hydrocarbon-soluble exchange reagents according to claim 1 with halogenated or thiolate-functionalized aromatics or heteroaromatics of the general formulas Hal-Ar, Hal-HetAr, $R^9S$—Ar, or $R^9$S-HetAr wherein $R^9$=alkyl or aryl and reacting electrophiles with the metalated intermediates Ar—Mg—$OR^3$.$LiOR^2$.aDonor, HetAr—Mg—$OR^3$.$LiOR^2$.aDonor, $Ar_2Mg.LiOR^2.LiOR^3$.aDonor and $HetAr_2Mg.LiOR^2.LiOR^3$.aDonor for CC or CN coupling reactions or addition reactions.

12. The process of claim 11 wherein the halogenated or thiolate-functionalized aromatics or heteroaromatics have one or several functional groups selected from the group consisting of F, Cl, Br, CN, $CO_2R$, OR, OH, $NR_2$, NHR, $NH_2$, $PR_2$, $P(O)R_2$, $CONR_2$, CONHR, SR, SH, $CF_3$, $NO_2$.

13. A process comprising reacting the hydrocarbon-soluble exchange reagents according to claim 1 in exchange reactions with electron-rich aromatics.

14. The process of claim 12 wherein the electron-rich heteroaromatics are selected from the group consisting of pyrroles, furans, thiophenes, oxazoles, isoxazoles, thiazoles, isothiazoles, imidazoles, benzimidazoles, triazoles, indazoles, and indoles.

15. The process of claim 11 wherein the halogenated aromatics or heteroaromatics are selected from the group consisting of: bromobenzene, bromotoluenes, bromoanisoles, bromo-N,N-dimethylanilines, 1-bromo-3,5-dimethoxybenzene, bromonaphthalenes, bromophenanthrenes, bromothiophenes, bromopyridines, bromobenzothiophenes, bromobenzofurans, 1,2-dibromocyclopent-1-ene, tert-butyl 2-(methylthio)piperidine-1-carboxylate, tert-butyl 2-(phenylthio)piperidine-1-carboxylate, tert-butyl 4-methyl-2-(phenylthio)piperidine-1-carboxylate, tert-butyl 2-((4-methoxyphenyl)thio)piperidine-1-carboxylate, tert-butyl 2-((4-fluorophenyl)thio)piperidine-1-carboxylate, tert-butyl 2-(phenylthio)pyrrolidine-1-carboxylate, and 2-(phenylthio)pyridine.

\* \* \* \* \*